US010062356B1

(12) United States Patent
Krasowski et al.

(10) Patent No.: US 10,062,356 B1
(45) Date of Patent: Aug. 28, 2018

(54) TWO AND THREE DIMENSIONAL NEAR INFRARED SUBCUTANEOUS STRUCTURE IMAGER USING REAL TIME NONLINEAR VIDEO PROCESSING

(75) Inventors: Michael J Krasowski, Chargin Falls, OH (US); Joseph M Flatico, Lakewood, OH (US); Phillip P Jenkins, Cleveland Heights, OH (US); Lawrence C Greer, Avon, OH (US)

(73) Assignee: The United States of America as Represented by the Admin of National Aeronautics and Space Administration, Washington, DC (US)

( * ) Notice: Subject to any disclaimer, the term of this patent is extended or adjusted under 35 U.S.C. 154(b) by 642 days.

(21) Appl. No.: 12/285,157

(22) Filed: Sep. 30, 2008

(51) Int. Cl.
*G01J 1/44* (2006.01)
*G09G 5/10* (2006.01)
*H04N 5/33* (2006.01)
*G01J 5/20* (2006.01)

(52) U.S. Cl.
CPC ............ *G09G 5/10* (2013.01); *G01J 1/44* (2013.01); *H04N 5/33* (2013.01); *G01J 5/20* (2013.01)

(58) Field of Classification Search
CPC ..... H04N 5/33; G01J 5/20; G01J 1/44; G09G 5/10
See application file for complete search history.

(56) References Cited

U.S. PATENT DOCUMENTS

| 4,817,622 | A | | 4/1989 | Pennypacker et al. |
| 4,980,756 | A | * | 12/1990 | Lagoni ............... H04N 5/57 |
| | | | | 348/675 |
| 5,148,809 | A | | 9/1992 | Biegeleisen-Knight et al. |
| 5,512,958 | A | * | 4/1996 | Rzeszewski ............ 348/607 |
| 5,608,210 | A | | 3/1997 | Esparza et al. |
| 6,120,461 | A | * | 9/2000 | Smyth ..................... 600/558 |
| 6,178,340 | B1 | | 1/2001 | Svetliza |
| 6,230,046 | B1 | | 5/2001 | Crane |
| 6,556,858 | B1 | | 4/2003 | Zeman |
| 6,584,340 | B1 | | 6/2003 | Horiuchi |
| 7,239,909 | B2 | | 7/2007 | Zeman |
| 7,381,953 | B1 | | 6/2008 | Kaufman |
| 7,415,139 | B2 | | 8/2008 | Takiguchi |
| 7,952,557 | B2 | * | 5/2011 | Amundson et al. ......... 345/107 |
| 2004/0215081 | A1 | | 10/2004 | Crane et al. |
| 2005/0014995 | A1 | | 1/2005 | Amundson et al. |
| 2005/0228265 | A1 | | 10/2005 | Robertson et al. |
| 2007/0038118 | A1 | | 2/2007 | DePue et al. |
| 2008/0122857 | A1* | | 5/2008 | Hsuan ..................... 345/589 |

(Continued)

FOREIGN PATENT DOCUMENTS

WO     WO 2006128648 A2 * 12/2006

*Primary Examiner* — David Porta
*Assistant Examiner* — Carolyn Igyarto
(74) *Attorney, Agent, or Firm* — Robert H. Earp, III; William M. Johnson (57) ABSTRACT

An imager is provided for viewing subcutaneous structures. In an embodiment of the invention, the imager includes a camera configured to generate a video frame, and an adaptive nonlinear processor. The adaptive nonlinear processor is configured to adjust a signal of the video frame below a first threshold to a maximum dark level and to adjust the signal of the video frame above a second threshold to a maximum light level. The imager further includes a display, configured to display the processed video frame.

17 Claims, 5 Drawing Sheets

(56) References Cited

U.S. PATENT DOCUMENTS

2008/0135757 A1     6/2008   D'Souza et al.
2008/0194930 A1     8/2008   Harris et al.
2008/0266669 A1*   10/2008   Durner et al. ................ 359/630

\* cited by examiner

TWO AND THREE DIMENSIONAL NEAR INFRARED SUBCUTANEOUS STRUCTURE IMAGER USING REAL TIME NONLINEAR VIDEO PROCESSING

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

Field of the Invention

The present invention relates generally to imaging systems, and particularly near-infrared imaging systems.

Description of the Related Art

In a clinical setting, the locating of subcutaneous structures, such as veins, for needle insertion can often be problematic. For example, small veins in pediatric patients, or veins in very dark-skinned or obese people, can be difficult to see or palpate. In emergency situations, such as accident sites, or battlefield situations, the need to locate a subcutaneous vessel, or a vessel exposed in a wound site, can arise unexpectedly. Thus, under-skilled persons may be called upon to access a subcutaneous vessel, for example, to insert a needle, or to tie off a bleeder. Thus, an imager that allows a user to view the subcutaneous vessel is needed.

Present subcutaneous vessel imagers use large, multiple, and often separate assemblies with complicated optics to image subcutaneous structures as two-dimensional maps on a wide monitor, or as maps extracted by a computer and focused onto the skin by a video projection. Furthermore, due to the scattering of the infrared light, veins imaged by prior art methods appear shadowy and distorted. Thus, an imager which allows a user to view subcutaneous structures and produce two-dimensional or three-dimensional images, yet which is still compact and inexpensive, is needed.

SUMMARY OF THE INVENTION

Some embodiments of the invention can provide an apparatus, which includes a first camera configured to generate a video frame. The apparatus further includes a processor, operatively connected to the first camera, configured to adjust a signal of the video frame that is below a threshold to a maximum dark level and to adjust the signal of the video frame that is above the threshold to a maximum light level. The apparatus further includes a display, operatively connected to the processor, configured to display the video frame.

Furthermore, some embodiments of the invention can provide a system, which includes a first camera configured to generate a video frame. The system further includes a processor, operatively connected to the first camera, configured to adjust a signal of the video frame that is below a threshold to a maximum dark level and to adjust the signal of the video frame that is above the threshold to a maximum light level. The system further includes a display, operatively connected to the processor, configured to display the video frame.

Furthermore, some embodiments of the invention can provide a method for generating an image of a subcutaneous structure. The method includes the step of receiving a video frame from a first camera configured to generate the video frame. The method further includes the step of adjusting a signal of the video frame that is below a threshold to a maximum dark level. The method further includes the step of adjusting the signal of the video frame that is above the second threshold to a maximum light level. The method further includes the step of sending the video frame to a display configured to display the video frame.

Furthermore, some embodiments of the invention can provide a computer readable medium, encoded with a computer program, for controlling a processor to implement a method. The method includes receiving a video frame from a first camera configured to generate the video frame. The method further includes adjusting a signal of the video frame that is below a threshold to a maximum dark level. The method further includes adjusting the signal of the video frame that is above the second threshold to a maximum light level. The method further includes sending the video frame to a display configured to display the video frame.

Furthermore, some embodiments of the invention can provide an apparatus, which includes a video input circuit configured to receive a video signal. The apparatus further includes a black level clamp configured to set a portion of the video signal to a maximum dark level. The apparatus further includes a video amplitude gain adjust circuit configured to set a portion of the video signal to a maximum light level. The apparatus further includes a maximum value circuit configured to adjust the video signal that is below a threshold to the maximum dark level. The apparatus further includes a gain difference amplifier circuit configured to adjust the video signal that is above a threshold to the maximum light level. The apparatus further includes a video output circuit configured to send the video signal.

Furthermore, some embodiments of the invention can provide an apparatus, which includes camera means for generating a video frame. The apparatus further includes processor means for adjusting a signal of the video frame that is below a threshold to a maximum dark level and for adjusting the signal of the video frame that is above the threshold to a maximum light level, The apparatus further includes display means for displaying the video frame.

Furthermore, some embodiments of the invention can provide an apparatus, which includes video input means for receiving a video signal. The apparatus further includes clamping means for setting a portion of the video signal to a maximum dark level. The apparatus further includes gain adjust means for setting a portion of the video signal to a maximum light level. The apparatus further includes maximum value means for adjusting the video signal that is below a threshold to the maximum dark level. The apparatus further includes gain difference amplifier means for adjusting the video signal that is above a threshold to the maximum light level. The apparatus further includes video output means for sending the video signal.

BRIEF DESCRIPTION OF THE DRAWINGS

For proper understanding of the invention, reference should be made to the accompanying drawings, wherein.

DETAILED DESCRIPTION OF THE PREFERRED EMBODIMENT(S)

It will be readily understood that the components of the present invention, as generally described and illustrated in the figures herein, may be arranged and designed in a wide variety of different configurations. Thus, the following detailed description of the embodiments of an apparatus, a system, a method, and a computer readable medium, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with the embodiment may be included in at least one embodiment of the present invention. Thus, appearances of the phrases "in certain embodiments," "in some embodiments," "in other embodiments," or other similar language, throughout this specification do not necessarily all refer to the same group of embodiments, and the described features, structures, or characteristics may be combined in any suitable manner in one or more embodiments.

An innovative near-infrared imager which provides a high contrast visualization of subcutaneous structures is described. Utilizing this innovative near-infrared imager, an operator can see subcutaneous structures with a sense of location and depth. This imager may operate in complete darkness and is not impeded by melanin in the skin. The imager may be useful for the locating of veins and other structures for access, such as needle insertion or excision. The imager can operate as either a two-dimensional imager or a three-dimensional imager.

The imager includes an adaptive nonlinear processor to increase image contrast. According to embodiments of the invention, video frames are passed through the processor which may drive dark levels before a certain threshold to a maximum black level. The processor may then adjust the gain for signals above this level to stretch the video to a maximum white level. This function may allow the user of the imager to make a subcutaneous structure (such as a vein) the darkest feature in the image, while stretching the remaining gray levels toward the white.

Figure 1:
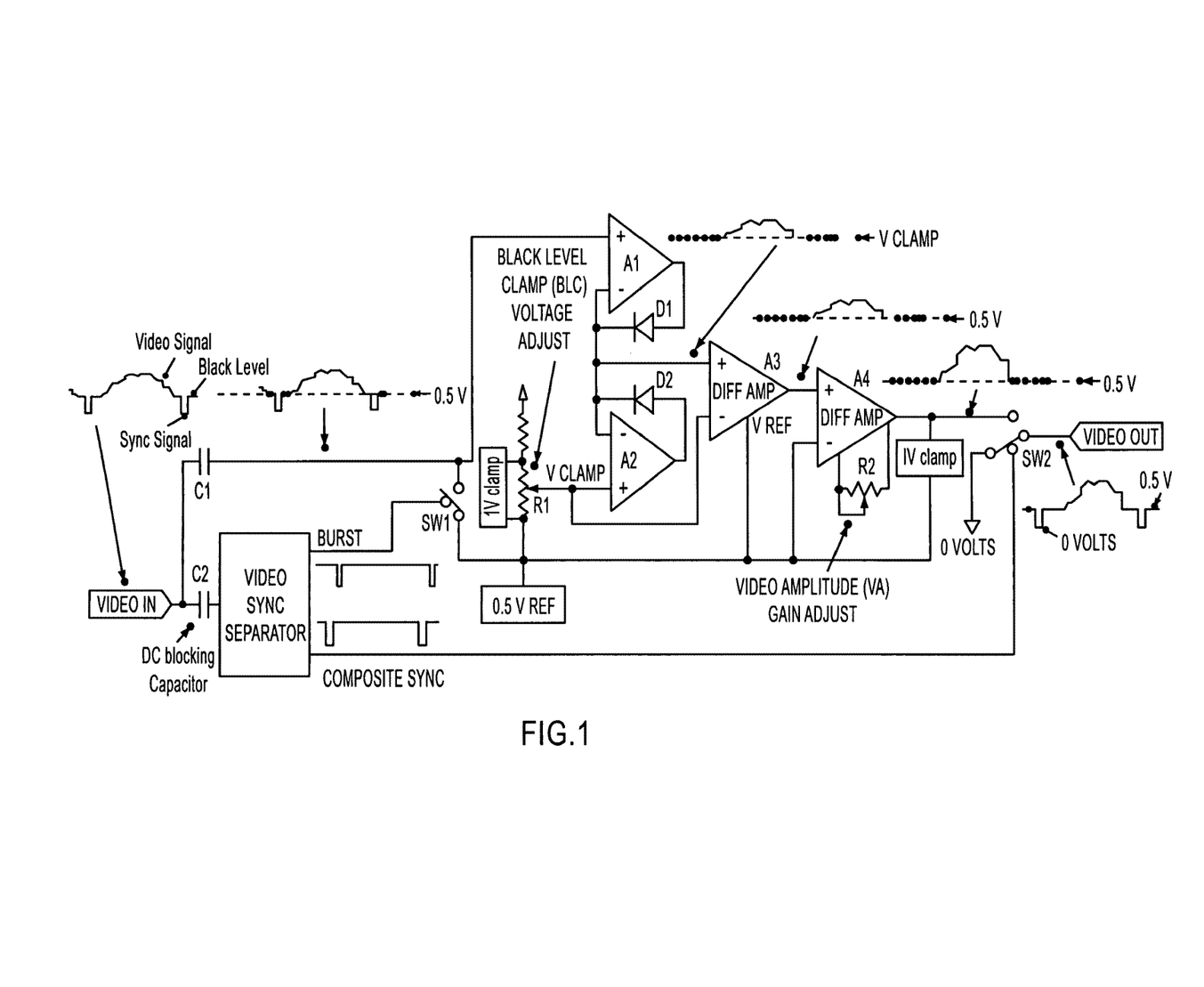
FIG. 1 illustrates an example embodiment of an adaptive nonlinear processor according to an embodiment of the present invention.

FIG. 1 is a block diagram which illustrates an example embodiment of an adaptive nonlinear processor, according to an embodiment of the present invention.

The depicted adaptive nonlinear processor may include a video in component, which receives a video signal. The video signal may be any type of composite video (for example RS-170). Composite video is a format of an analog video signal. Composite video is also referred to as "Color, Video, Blank and Sync" or CVBS. A composite video signal is a composite of three source signals called Y, U, and V (together referred to as YUV), and also includes synch pulses. A synch pulse is a negative-going timing pulse used to synchronize the horizontal and vertical portions of the display. A composite video signal is usually in a standard format such as National Television System Committee (NTSC), Phase Alternating Line (PAL), and Séquentiel Couleur à Mémoire (i.e. Sequential Color With Memory) (SECAM).

A portion of a composite video signal that makes up one horizontal scan line of a picture includes an active video portion and a horizontal blanking position.

The horizontal blanking portion includes a front porch portion, a sync tip portion, a breezeway portion, a color burst portion, and a black porch portion. The front porch is the beginning of the composite video signal (or the area which occurs right after the end of the active video portion) and occurs before the leading edge of the synch pulse. The sync tip is the area of the composite video signal which includes the synch pulse. The breezeway is the area of the composite video signal defied as the time between the rising edge of the sync pulse and the start of the color bust. The color burst, also known as the color subcarrier, is 8 to 10 cycles of a color reference frequency. It is positioned between the rising edge of the sync pulse, and the start of the active video portion of the composite video signal. Finally the back porch is the area of the composite video signal between the end of the color burst and the start of the active video portion.

The active video portion contains the picture brightness (luma) and color (chroma) information. The brightness information is the instantaneous amplitude at any point in time. Color information is added on top of the luma signal and is a sine wave with the colors identified by a specific phase difference between it and a color burst reference phase. An amplitude of the modulation is proportional to the amount of color (or saturation), and the phase information denotes the tint (or hue) of the color.

In certain embodiments of the invention, the video signal of FIG. 1 may have embedded synchronization pulses, as well as a black level at a back porch. In certain embodiments, the video signal has the following values:
White: +1.000 V
Black: +0.075 V
Blank: 0 V
Sync: −0.400 V The depicted adaptive nonlinear processor may include DC-blocking capacitors C1 and C2, and a video sync separator circuit, video sync separator. C1 and C2 block the DC component of the video signal, creating one path through C2 to the video synch separator, and one path through C1 to the video circuitry. The video sync separator circuit creates a pulse train, identified in FIG. 1 as composite synch, which is coincident to the position of the horizontal and vertical synch pulses, and another pulse train, identified in FIG. 1 as burst, which is coincident to the area on the back porch which is at the black level.

The depicted adaptive nonlinear processor may include switch SW1. According to the embodiment of the invention, after the video signal has passed through capacitor C1, its DC back level is clamped to the on circuit 0.5 volt reference voltage, identified in FIG. 1 as 0.5 V REF by shorting the circuit side of C1 to voltage 0.5 V REF through switch SW1 during the back porch portion of the video signal. Thus, 0.5 volts DC is stored on the circuit side of C2, and thus biases the video signal. Droop is minimal, as this voltage is refreshed after each and every sync pulse.

The resulting video signal now has its black level biased to 0.5 volts DC and is passed on to the maximum value circuit for black level clamping. A clamp is a circuit that forces a specific portion (either the back porch or the sync tip) of the video signal to a specific DC voltage, to restore the DC level. The black level clamp forces the back-porch voltage to be equal to the voltage produced by the potentiometer identified in FIG. 1 as black level clamp (BLC) voltage adjust.

The potentiometer, black level clamp (BLC) voltage adjust, produces a voltage, identified in FIG. 1 as v clamp. The voltage v clamp, rides above voltage 0.5 V REF, but is biased below some upper voltage such that the range of voltage v clamp is approximately 0.5 V REF to (1+0.5 V REF). This satisfies a full video white level of +1.000 V above Blank, as noted above.

The resulting video signal is also passed to a maximum value circuit. In the embodiment depicted in FIG. 1, the maximum value circuit is represented by amplifiers A1 and A2, and diodes D1 and D2. However, one of ordinary skill in the art would readily understand that this circuit topography is merely an example of the maximum value circuit, and that the maximum value circuit could be represented by other circuit topographies, in alternative embodiments, and be consistent with the invention. Thus, the circuit topography of the maximum value circuit is not limited to the circuit topography displayed in FIG. 1.

According to the embodiment of the invention, the amplifier A1 and the diode D1 handle the video signal, while the amplifier A2 and the diode D2 handle the voltage v clamp. Together, the output of the maximum value circuit, given as the node comprising the inverting inputs of both A1 and A2, and the cathodes of D1 and D2, will be the maximum of the two inputs, the video signal and the voltage v clamp. For example, if the voltage v clamp is set to 0.8 volts above voltage 0.5 V REF, then all video signal components below 0.8 volts above voltage 0.5 V REF will be suppressed, and the output of this maximum value circuit shall be 0.8 volts. If any components of the incoming video signal are above 0.8 volts above voltage 0.5 V REF, then the output of this maximum value circuit shall be the values of that incoming video signal exceeding 0.8 volts over voltage 0.5 V REF. Thus, setting voltage v clamp also sets where the useable incoming video signal shall start.

The depicted adaptive nonlinear processor may also include a unit gain difference amplifier. The difference amplifier is identified in FIG. 1 as amplifier A3. However, one of ordinary skill in the art would readily understand that this circuit topography is merely an example of the unit gain difference amplifier, and that the unit gain difference amplifier could be represented by other circuit topographies, in alternative embodiments, and be consistent with the invention. Thus, the circuit topography of the unit gain difference amplifier is not limited to the circuit topography displayed in FIG. 1.

According to the embodiment of the invention, the reference of amplifier A3 is voltage 0.5 V REF. The output of the maximum value circuit is routed to the positive input of amplifier A3, while voltage v clamp is routed to its negative input. Thus, the output of this amplifier is the output of the maximum value circuit minus voltage v clamp, referenced to voltage 0.5 V REF. In other words, the output of amplifier A3 is voltage 0.5 V REF, plus the output of the maximum value circuit minus voltage v clamp. Thus, the output of amplifier A3 is the video signal where all the amplitude components are above voltage v clamp, and riding atop of voltage 0.5 V REF.

Thus, according to the embodiment of the invention, the contrast of the video signal may be adjusted. Specifically, the black level of the video signal may be adjusted.

The depicted adaptive nonlinear processor may also include a variable gain difference amplifier. The difference amplifier is identified in FIG. 1 as amplifier A4. However, one of ordinary skill in the art would readily understand that this circuit topography is merely an example of the variable gain difference amplifier, and that the variable gain difference amplifier could be represented by other circuit topographies, in alternative embodiments, and be consistent with the invention. Thus, the circuit topography of the variable gain difference amplifier is not limited to the circuit topography displayed in FIG. 1.

According to the embodiment of the invention, the lowest possible gain of amplifier A4 is unity, and the upper gain limit of amplifier A4 is sufficient to stretch the video signal after clamp and maximum value processing up to BLANK plus +1.000 volts. The output of amplifier A4 is clamped such that if the output of amplifier A4 attempts to exceed BLANK plus +1.000 volts, its output is clamped to BLANK plus +1.000 volts. This is done to stay within specifications for video standards, and not stress display devices. Thus, as an example, if after clamp and maximum value processing, the maximum video amplitude component is BLANK plus 0.5 volts, and a user desires more brightness, the user may adjust the gain of amplifier A4 towards a value of two to move the resulting video signal amplitude component toward BLANK plus +1.000 volts. This adjustment to the gain value is done by a potentiometer, identified in FIG. 1 as video amplitude (VA) gain adjust. Since the negative input of amplifier A4 is based on voltage 0.5 V REF, the resulting signal is the amplified version of the output of amplifier A3, also referenced to voltage 0.5 V REF.

The depicted adaptive nonlinear processor may include switch SW2. SW2 is a single pole dual throw switch, whose position is controlled by composite sync. When composite sync is high, signifying blank, black, or video, the video signal output from amplifier A4 is passed onto the display device, biased to voltage 0.5 V REF. When composite sync is low, signifying the presence of a sync pulse, the switch is controlled to pass 0 volts. Thus, the outgoing video signal has sync tips that are consistent with Sync: −0.400 V.

Thus, according to the embodiment of the invention, the depicted adaptive nonlinear processor may adjust the contrast of the video signal by clamping the video signal so that the black levels below a first threshold appear black when displayed. Furthermore, according to the embodiment of the invention, the depicted adaptive nonlinear processor may further adjust the contrast of the video signal by adjusting the gain of the video signal so that the resulting gray levels above a second threshold are stretched to white, so that the resulting gray levels appear whiter when displayed. Accordingly, the depicted adaptive nonlinear processor may adjust the incoming video signal's contrast and brightness to create a nonlinear transfer function which produces and image wherein the feature of choice, for example, the subcutaneous structure, may be presented maximally contrasted against background brightness.

According to certain embodiments of the invention, the first and second thresholds may be automatically established by the imager. However, in alternative embodiments of the invention, the thresholds may be established by the user. Furthermore, in alternatives embodiments of the invention, the user may adjust the thresholds to further adjust the contrast of the displayed image.

In the depicted embodiment of the invention, the adaptive nonlinear processor may have one breakpoint for the piecewise linear approximation to a nonlinear transfer function to adjust the contrast and the brightness of the incoming video signal. However, in alternative embodiments, more breakpoints may be easily added through replication of the maximum value circuit and gain circuits shown in FIG. 1 to create a piecewise linear approximation to any desired nonlinear transfer function. These breakpoints may be manipulated manually, manipulated automatically, fixed, or any combination of the three.

As described above, the adaptive nonlinear processor of the invention may be utilized in various embodiments of the imager. Exemplary embodiments of the imager are described below in more detail.

Figure 2:
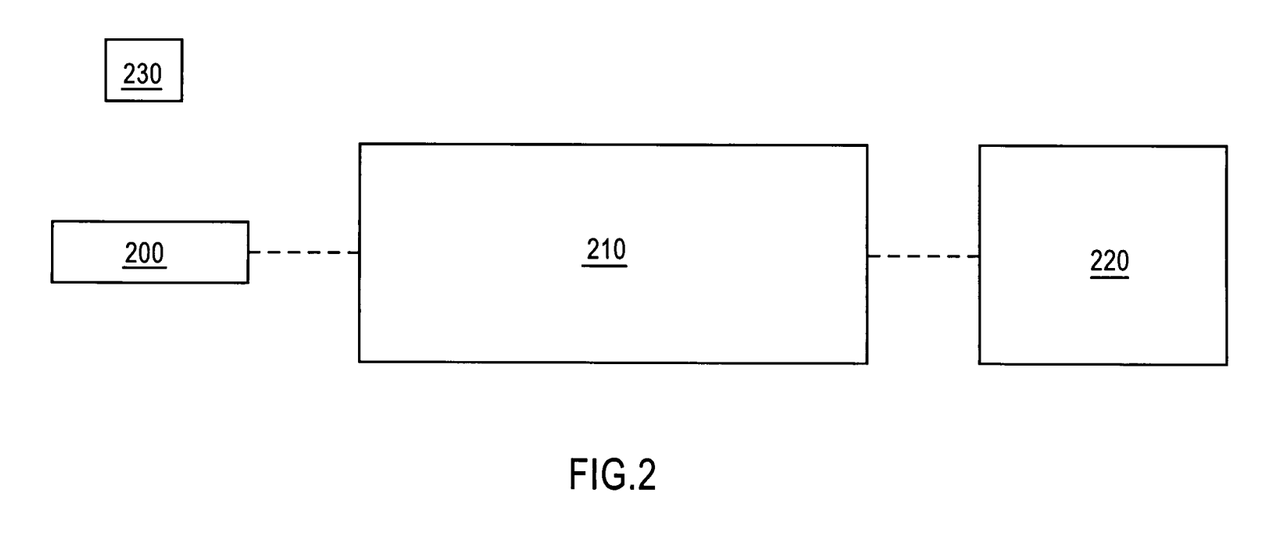
FIG. 2 illustrates another example embodiment of an imager according to an embodiment of the present invention.

FIG. 2 illustrates an example embodiment of an imager which utilizes an adaptive nonlinear processor according to the present invention. The imager includes camera 200, adaptive nonlinear processor 210, and display 220. Camera 200 may be configured to produce a video signal. The adaptive nonlinear processor 210 may be configured to receive the video signal from the camera 200, and to process the video signal by adjusting the contrast of the video signal, as described in relation to the adaptive nonlinear processor of FIG. 1. In certain embodiments, the adaptive nonlinear processor 210 corresponds to an adaptive nonlinear processor as depicted in FIG. 1. The display 220 may be configured to display the video signal which is output by the adaptive nonlinear processor 210.

In this exemplary embodiment, the adaptive nonlinear processor 210 may receives the video frame from one camera. Thus display 220 may display a two-dimensional image of a subcutaneous structure for the user. In certain embodiments, the adaptive nonlinear processor 210 may be embedded within the camera 200.

Furthermore, according to certain embodiments, camera 200 may include a low-power complementary metal oxide semiconductor (CMOS) single-chip imager. Camera 200 may also include an optical lens and a filter according to certain embodiments. The optical lens and filter of each camera may be optimized for near-infrared light with a wavelength range of 940 to 950 nanometers.

In certain embodiments, the camera 200 is a NTSC camera, which is configured to output a NTSC composite video signal. However, one of ordinary skill in the art would readily understand that the processor may work with any type of camera, and may work with any format of composite video (such as PAL, and SECAM).

According to the embodiment of the invention, the display 220 of the imager may be any display which accepts NTSC video signals. According to certain embodiments, the display 220 of the imager may be a virtual reality headset. In certain embodiments, camera 220 is affixed to an adjustable binocular assembly mounted to the front of the virtual reality headset display. The virtual reality headset display may display a two-dimensional image produced by camera 200 and adaptive nonlinear processor 210.

According to certain embodiments, the imager may include an illuminator 230. The illuminator is configured to illuminate the site that camera 200 is viewing. In certain embodiments, the illuminator may be mounted to camera 200. However, one of ordinary skill in the art would readily understand that in alternative embodiments, the illuminator 230 may be a separate, stand-alone component. Furthermore, one of ordinary skill in the art would readily understand that the imager may function using natural light, without the aid of an illuminator. Thus, while the embodiment of the imager depicted in FIG. 2 includes an illuminator, in other alternative embodiments of the invention, the imager may not include an illuminator.

The use of illuminator 230 may allow the imager to penetrate the skin and view subcutaneous structures in greater detail. In certain embodiments, illuminator 230 may include, for example, one or more of infrared light-emitting diodes. Infrared light may be useful in penetrating the skin and viewing the subcutaneous structure. In alternative embodiments, illuminator 230 may comprise a quartz halogen lamp. A quart halogen lamp is also very rich in near infrared-light, and may allow subcutaneous structures to stand out, with the subcutaneous structure appearing very black in contrast to the skin, which appears very white.

Furthermore, in certain embodiments, the illuminator 230 may be configured to emit near-infrared light with a wavelength of a range from 940 to 950 nanometers. A wavelength of a range from 940 to 950 nanometers may be optimal, since the wavelength penetrates the skin well, melanin at that wavelength, the CMOS imager of the camera 200 is very sensitive at that wavelength, and that certain types of blood (such as blood with reduced hemoglobin values) absorbs light strongly at that wavelength.

According to the embodiment depicted in FIG. 2, camera 200, adaptive nonlinear processor 210, and display 220 may be separate components, which may be operatively connected. However, one of ordinary skill in the art would readily understand that in alternative embodiments, camera 200, adaptive nonlinear processor 210, and display 220 may be physically connected as an integrated structure. For example, a portable handheld, battered powered device with an embedded illuminator, camera and display is consistent with the spirit and scope of the invention.

Figure 3:
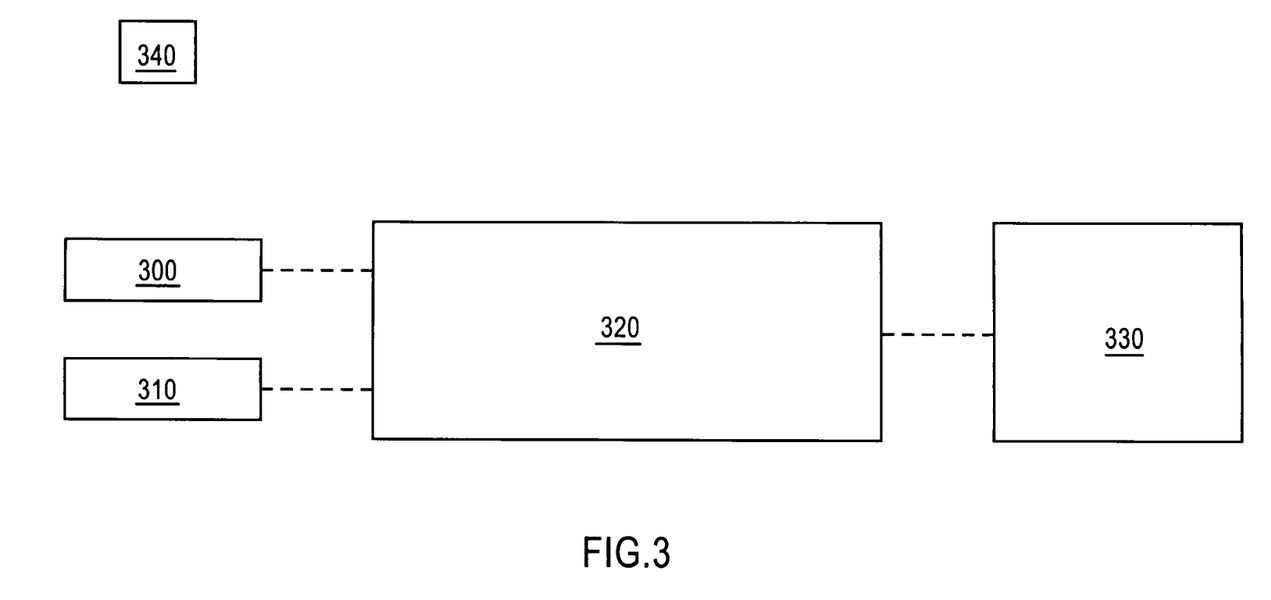
FIG. 3 illustrates another example embodiment of an imager according to an embodiment of the present invention.

FIG. 3 illustrates an example embodiment of an imager which utilizes an adaptive nonlinear processor according to the present invention. In this exemplary embodiment, the imager includes a first camera 300 and a second camera 310. Cameras 300 and 310 may each configured to produce a video signal. According to certain embodiments of the invention, cameras 300 and 310 may each correspond to camera 200 as depicted in FIG. 2.

The imager also includes an adaptive nonlinear processor 320. The adaptive nonlinear processor 320 may be configured to receive the video signal from the cameras 300 and 310, and to process the video signal by adjusting the contrast of the video signal, as described in relation to the adaptive nonlinear processor of FIG. 1. In certain embodiments, the adaptive nonlinear processor 320 corresponds to an adaptive nonlinear processor as depicted in FIG. 1. The imager also includes a display 330 configured to display the video signal which is output by the adaptive nonlinear processor 320.

Because the embodiment of the invention depicted in FIG. 3 includes two cameras, as opposed to one camera as shown in the embodiment of the invention depicted in FIG. 2, the manner in which the cameras 300 and 310 provide the video signal may be utilized to produce a three-dimensional image of a subcutaneous structure.

The manner in which cameras 300 and 310 may provide the video signal to the adaptive nonlinear processor 320 will now be discussed in more detail, according to an embodiment of the invention. A NTSC camera normally produces an odd and even field of a video frame. A standard NTSC video signal is divided into odd and even fields every $1/60$th of a second, with the second field interlaced or vertically offset between the scan lines of the first, to produce a complete image every $1/30$th of a second. An identity of the field tells the monitor, camera, or other video device, whether the current field contains the odd or even scan lines. This is known as generation locking or genlocking.

According to certain embodiments of the invention, the genlocking of two images with odd/even field multiplexing is replaced with left/right camera multiplexing, so that cameras 300 and 310 both produce their even field at the same time, and both produce their odd field at the same time. Thus, according to certain embodiments of the invention, cameras 300 and 310 may be multiplexed such that first camera 300 and second camera 310 each supply a separate field of the video frame to the adaptive nonlinear processor 320. This ultimately produces a stereoscopic image which can be displayed by display 330. The stereoscopic image may produce a three-dimensional image to the user who views display 230.

According to certain embodiments of the invention, display 330 may correspond to display 200 as depicted in FIG. 2. Furthermore, according to certain embodiments, the display 330 of the imager may be a virtual reality headset. In certain embodiments, cameras 300 and 310 are affixed to an adjustable binocular assembly mounted to the front of the virtual reality headset display. The virtual reality headset display is configured to display the fields from first camera 300 to the left eye of a user and those from second camera 310 to the right eye of the user. Thus, the virtual reality headset display may display a three-dimensional image based on the stereoscopic image produced by the multiplexing of cameras 300 and 310.

According to certain embodiments, the imager may include an illuminator 340 According to certain embodiments of the invention, illuminator 340 may correspond to illuminator 230 as depicted in FIG. 2.

According to the embodiment depicted in FIG. 2, cameras 300 and 310, adaptive nonlinear processor 320, and display 330 may be separate components, which may be operatively connected. However, one of ordinary skill in the art would readily understand that in alternative embodiments, cameras 300 and 310, adaptive nonlinear processor 320, and display 330 may be physically connected as an integrated structure.

Figure 4:
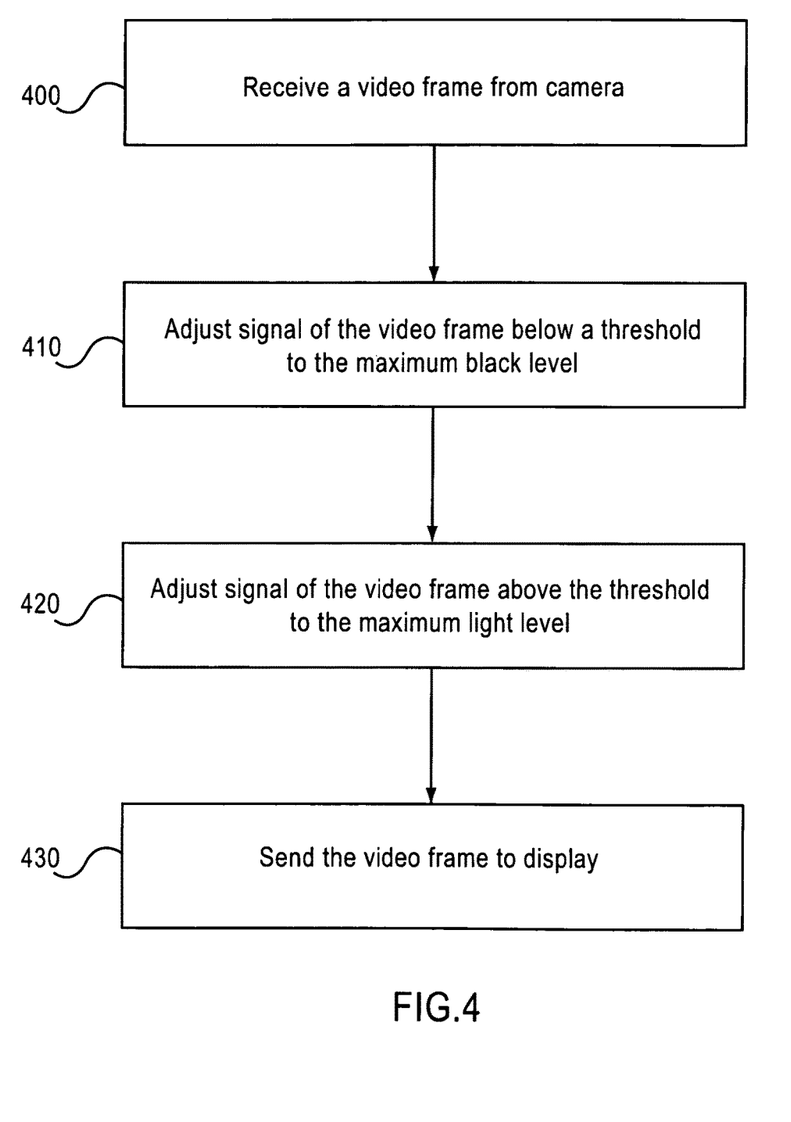
FIG. 4 illustrates a method, in accordance with another embodiment of the present invention.

FIG. 4 is a method for generating an image of a subcutaneous structure, in accordance with an embodiment of the invention. At step 400, a video frame is received from a camera configured to generate the video frame. At step 410, the signal of the video frame is adjusted below a threshold to a maximum dark level. At step 420, the signal of the video frame is adjusted above the threshold to a maximum light level. At step 430, the video frame is sent to a display configured to display the video frame. Thus, according to the embodiment of the invention, the method may produce a two-dimensional image of a subcutaneous structure.

Figure 5:
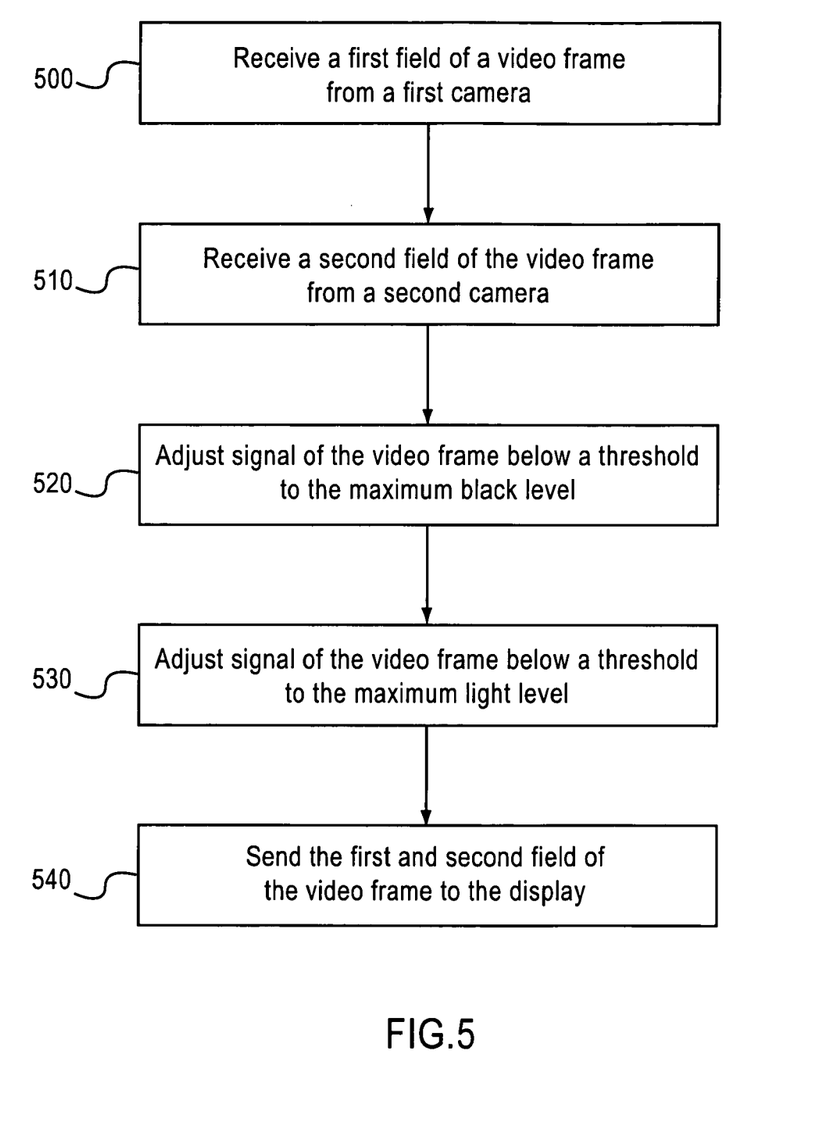
FIG. 5 illustrates another method, in accordance with another embodiment of the present invention.

FIG. 5 is a method for generating an image of a subcutaneous structure, in accordance with another embodiment of the invention. At step 500, a first field of a video frame is received from a first camera. At step 510, a second field of a video frame is received from a second camera. At step 520, a signal of the video frame is adjusted below a threshold to a maximum dark level. At step 530, the signal of the video frame is adjusted above the threshold to a maximum light level. At step 540, the video frame is sent to a display configured to display the first field of the video frame and the second field of the video frame. Thus, according to the embodiment of the invention, the method may produce a three-dimensional image of a subcutaneous structure.

The method steps performed in FIG. 4 and FIG. 5 may be performed by a computer program product, encoding instructions for the nonlinear adaptive processor to perform at least the method described in FIG. 4 and the method described in FIG. 5, in accordance with an embodiment of the present invention. The computer program product may be embodied on a computer readable medium. A computer readable medium may be, but is not limited to, a hard disk drive, a flash device, a random access memory, a tape, or any other such medium used to store data. The computer program product may include encoded instructions for controlling the nonlinear adaptive processor to implement the method described in FIG. 4, and the method described in FIG. 5, which may also be stored on the computer readable medium.

The computer program product can be implemented in hardware, software, or a hybrid implementation. The computer program product can be composed of modules that are in operative communication with one another, and which are designed to pass information or instructions to display. The computer program product can be configured to operate on a general purpose computer, or an application specific integrated circuit ("ASIC").

As described above, prior art subcutaneous vessel imagers use large, multiple, and often separate assemblies with complicated optics to image subcutaneous structures. In contrast, embodiments of the invention may be light-weight, inexpensive, and completely self-contained, may operate as a two- or three-dimensional imager, and may use an adaptive nonlinear processor to increase image contrast.

These features make embodiments of the invention useful for clinicians and field users alike. As staffing costs go up, and as hospitals and clinics strive to lower costs, more and more health professions are being called upon to cross-train. Embodiments of the invention may allow persons who are not trained as phlebotomists to quickly master the skills necessary to access veins. Furthermore, in the battlefield, embodiments of the invention may enable an individual service member to deliver medications or fluids intravenously with a greater possibility of success. The closed headset and the chosen illumination wavelength may combine to enable light discipline on the battlefield. Additionally, during an aircraft or spacecraft mission, intravenous access for drawing blood or infusion could be carried out by under-skilled personnel, thus allowing for a higher level of personnel health mitigation during flight. Finally, sub-surface lesions, especially heavily vascular sub-surface lesions, such as cancers, could be imaged by embodiments of the invention in any modest setting.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:
1. An apparatus, comprising:
a first camera configured to generate a composite first video signal;
an analog non-linear processor operatively connected to the first camera, the analog non-linear processor comprising:

a sync separator circuit configured to produce a burst sync and a composite sync to preserve the timing of all blanking level and sync pulse timing of the first video signal;

a first user adjustment potentiometer configured to permit a user to adjust a voltage threshold;

a clamp circuit configured to be activated by the burst sync and configured to set any portions of the first video signal below the threshold to a maximum dark level;

a difference amplifier circuit configured to adjust the maximum dark level to a black level voltage;

a second user adjustment potentiometer configured to permit the user to adjust gain such that portions of the first video signal which are above the threshold are adjusted to a maximum bright level to produce a processed video signal;

an analog switch circuit configured to be actuated by the composite sync and configured to combine the processed video signal with a sync tip voltage to produce a second composite video signal; and a display, operatively connected to the analog non-linear processor, configured to display the second composite video signal.

2. The apparatus of claim 1, wherein the display further comprises a virtual reality headset, and an adjustable binocular assembly mounted to the front of the virtual reality headset.

3. The apparatus of claim 1, wherein the first camera comprises a first imager.

4. The apparatus of claim 3, wherein the first imager comprises a CMOS imager chip.

5. The apparatus of claim 1, further comprising an illuminator configured to illuminate a site that the camera is viewing.

6. The apparatus of claim 5, wherein the illuminator is mounted on the camera.

7. The apparatus of claim 5, wherein the illuminator further comprises one or more infrared light-emitting diodes.

8. The apparatus of claim 5, wherein the illuminator is further configured to illuminate at a wavelength of a range of 940 to 950 nanometers.

9. The apparatus of claim 1, wherein the first camera is further configured to generate the composite first video signal using a NTSC format.

10. The apparatus of claim 1, wherein the apparatus is further configured to automatically set the threshold and the maximum bright level to a default value.

11. The apparatus of claim 1, wherein the first camera further comprises an optical lens and a filter.

12. The apparatus of claim 1, wherein the apparatus further comprises a second camera, wherein the first camera is configured to generate a first field of the composite first video signal, wherein the second camera is configured to generate a second field of the composite first video signal, and wherein the display is configured to display the first field and second field of the second composite video signal.

13. The apparatus of claim 12, wherein the display further comprises a virtual reality headset, and an adjustable binocular assembly mounted to the front of the virtual reality headset, and wherein the virtual reality headset is configured to display the first field of the second composite video signal to the left eye of the user and to display the second field of the second composite video signal to the right eye of the user.

14. The apparatus of claim 12, wherein the first camera comprises a first imager, and wherein the second camera comprises a second imager.

15. The apparatus of claim 14, wherein the first imager and the second imager each comprise a CMOS imager chip.

16. The apparatus of claim 12, wherein the first and second camera are each further configured to generate the first and second field of the composite first video signal using a NTSC format.

17. The apparatus of claim 12, wherein the first and second camera each further comprise an optical lens and a filter.

* * * * *